(12) United States Patent
Shin

(10) Patent No.: US 10,734,964 B2
(45) Date of Patent: Aug. 4, 2020

(54) APPARATUS AND METHOD FOR CONTROLLING PERSONALISED AUDIO FREQUENCY EQUALIZER

(71) Applicant: Eui Sang Shin, Seoul (KR)

(72) Inventor: Eui Sang Shin, Seoul (KR)

( * ) Notice: Subject to any disclaimer, the term of this patent is extended or adjusted under 35 U.S.C. 154(b) by 0 days.

(21) Appl. No.: 16/510,079

(22) Filed: Jul. 12, 2019

(65) Prior Publication Data
US 2020/0021262 A1 Jan. 16, 2020

(30) Foreign Application Priority Data
Jul. 13, 2018 (KR) .......................... 10-2018-0081696

(51) Int. Cl.
*H04R 25/00* (2006.01)
*H03G 5/16* (2006.01)
*A61B 5/12* (2006.01)
*H04R 3/04* (2006.01)
*H04R 29/00* (2006.01)

(52) U.S. Cl.
CPC .............. *H03G 5/165* (2013.01); *A61B 5/125* (2013.01); *H04R 3/04* (2013.01); *H04R 29/001* (2013.01); *H04R 2430/01* (2013.01)

(58) Field of Classification Search
CPC ........ H03G 5/165; H04R 3/04; H04R 29/001; H04R 2430/01; H04R 25/50; H04R 25/75; H04R 25/70; A61B 5/125; A61B 5/123
See application file for complete search history.

(56) References Cited

U.S. PATENT DOCUMENTS

2013/0279709 A1* 10/2013 Suzuki .................... A61B 5/123 381/57
2019/0356989 A1* 11/2019 Li ........................... H04R 25/50

\* cited by examiner

*Primary Examiner* — Ping Lee
(74) *Attorney, Agent, or Firm* — Paratus Law Group, PLLC

(57) ABSTRACT

Disclosed is a method of controlling a personalized audio frequency equalizer by an audio device for outputting a sound source The method includes: a user's age grasping step of grasping a user's age by inquiring the user's age; a user's hearing ability measurement step of measuring, for each frequency, the minimum audible volume; a personalized equalizer creation step of creating the personalized equalizer using a system test user hearing data (HTUHD) that the user may hear when a volume having a system test frequency is outputted, and an application test user hearing data (STUHD), which is a value of volume that the user may hear, while increasing a volume having an application test frequency; and a sound source output step of outputting a sound source through the personalized equalizer created at the personalized equalizer creation step.

6 Claims, 6 Drawing Sheets

APPARATUS AND METHOD FOR CONTROLLING PERSONALISED AUDIO FREQUENCY EQUALIZER

CROSS-REFERENCE TO RELATED APPLICATION

This application claims priority to Korean Patent Application No. 10-2018-0081696, filed on Jul. 13, 2018, which is hereby incorporated by reference in its entirety.

BACKGROUND

The present invention relates to an apparatus for controlling an audio frequency equalizer, and more specifically, to an apparatus for controlling a personalized audio frequency equalizer.

People are frequently exposed to various sounds during their lifetime. However, with the advent of modern techniques, particularly personal portable music devices and headsets, we are in danger of rapidly deteriorating our hearing ability. Despite regulations limiting the maximum volume output of these devices, many devices are able to emit volume exceeding 85 dB and may permanently damage hearing, and this is due to lack of awareness of volume size.

Therefore, cases of hearing impairment caused by earphones and headphones are often reported. Although personal music devices offer a user to listen to audio without harming other people since these audio playback devices are generally inserted in or tightly attached to the ears of the user, they cause subtle impairments in the user's hearing or lead to hearing loss in severe cases. Although the user himself or herself should reduce the output level to solve this problem, users enjoying music of a genre such as heavy metal, rock or disco listen to the music raising the output level in many cases and habitually set an output level of the audio in most cases, and it is difficult to listen to audio at a proper volume.

Moreover, since clarity of music is hindered in a situation where there is a considerable amount of environmental background noise, the user increases the total volume to a level similar to the noise, and if the user is not sensitive to a specific frequency, the user increases the overall volume, which may damage the hearing ability.

Particularly, if a user does not wear a headphone capable of ambient isolation, the user is easy to be exposed to environmental noises since the sounds leak into the ears. In addition, intensity of ambient noises should not be underestimated since the ambient noises reach 95 dB as a result of measurement at downtown subway stations. Although the volume alone may permanently damage the hearing ability, frequently, the user unconsciously increase the total volume at all frequencies to overcome the environmental noises, and loss of hearing is accelerated.

This problem can be solved by providing a separate equalizer so that the user may manually and digitally increase or decrease volume of individual frequencies.

However, the equalizer has a problem described below.

Since the user is not accustomed to an equalizer platform and the sound unit of decibel, it is difficult to edit a desired signature. In addition, considering the non-linearity in the increase of volume of in the decibel units, there may be an unintended problem such as excessively increasing the frequency due to manual handling of an unaccustomed equalizer. Therefore, there may be a side effect of permanently damaging hearing ability or preventing accurately representing intended sound. Furthermore, since the threshold of hearing (TOH) of a user is not considered, there is a problem of providing a distorted and degraded sound to the user.

Furthermore, a user having a hearing loss at a specific frequency may not hear the sound by the setting of an equalizer that is not edited for the specific frequency. Such as user will likely increase the volume of the audio output device, increasing the sound pressure level across all frequencies. This average increase in sound pressure level may still prevent the user from hearing the sound source of the frequency at which the hearing ability is lost. Further loss of hearing due to excessive sounds at the other frequencies may also occur.

In addition, a modern manual equalizer does not correctly transfer an audio intended by a creator to a user as is intended by a manufacturer. This is due to that the hearing curve of the user is uniquely deviated from the standard hearing data (SHD) across the entire audible spectrum of sound. That is, since the audio is not outputted as is heard, each user interprets the audio in a different way. Since the TOH of the user is not considered as described above, this problem can be solved only by the equalizer.

SUMMARY

Therefore, the present invention has been made in view of the above problems. The objective of the present invention is to provide an apparatus for controlling an audio frequency equalizer and a method thereof, which minimizes the difference between the hearing ability of a user and a standard hearing data (SHD) for the individual TOH of the user to supply a standard hearing ability to the user.

To accomplish the above objective, an aspect of the present invention provides a method of controlling a personalized audio frequency equalizer by an audio device for outputting a sound source, the method including: a user's age grasping step of identifying a user's age by inquiring the user's age; a user's hearing ability measurement step of measuring, for each frequency, the minimum volume required for the user to hear the given frequency; a personalized equalizer creation step of creating the personalized equalizer by comparing the system hardware test user hearing data (HTUHD), the data of the smallest system volume the user can hear per test frequency in a constant software volume unique per test frequency, against the application software test user hearing data (STUHD), the data of the smallest software volume the user can hear per test frequency in a constant system volume; and a sound source output step of outputting a sound source through the personalized equalizer created at the personalized equalizer creation step.

DESCRIPTION OF SYMBOLS

100: Apparatus for controlling Personalized audio frequency equalizer
110: User's hearing ability measurement unit
120: Personalized equalizer creation unit
130: Sound source output unit

DETAILED DESCRIPTION

The advantages and features of the present invention and a method for accomplishing them will be clarified with reference to the embodiments described below, together with the accompanying drawings. However, the present invention is not limited to the embodiments disclosed below and will be implemented in various different forms and provided to completely inform those skilled in the art of the scope of the present invention, and the present invention is defined only by the scope of the claims. In addition, in describing the present invention, if it is determined that the related known techniques may blur the gist of the present invention, detailed description thereof will be omitted.

Figure 1:
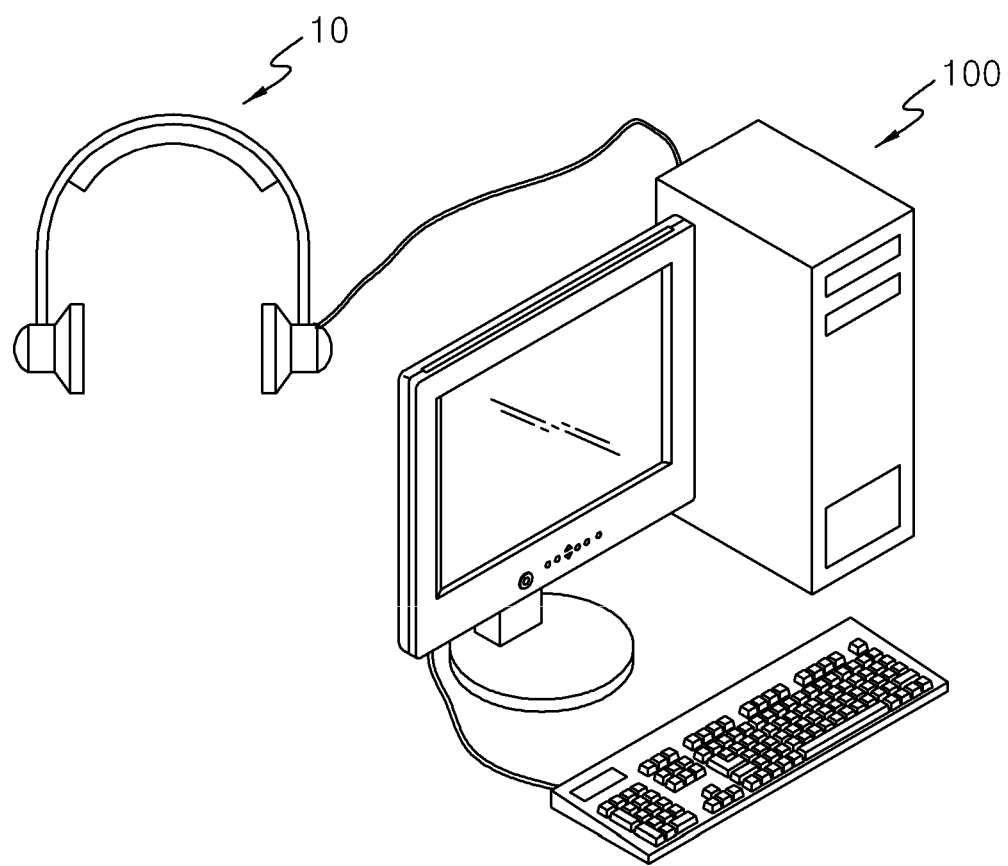
FIG. 1 is a perspective view showing an apparatus for controlling a personalized audio frequency equalizer according to an embodiment of the present invention.
Figure 2:
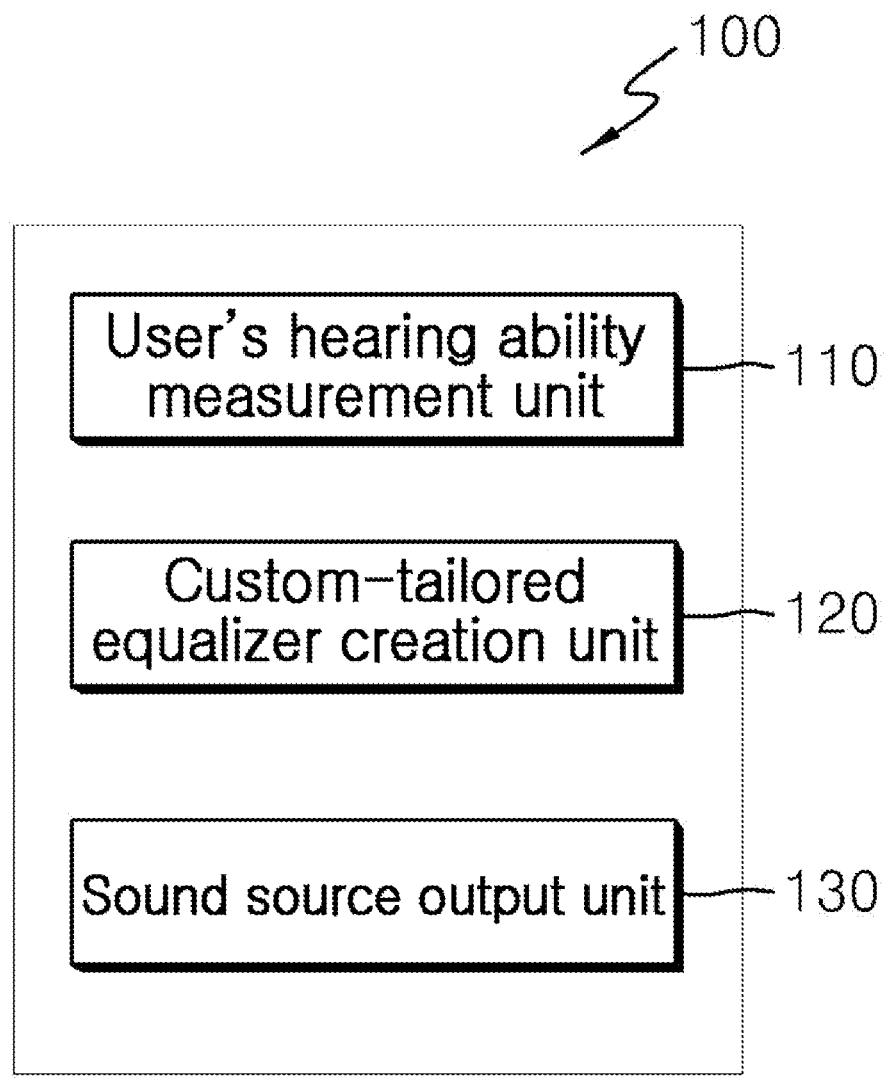
FIG. 2 is a block diagram showing the configuration of an apparatus for controlling a personalized audio frequency equalizer according to an embodiment of the present invention.
Figure 3:
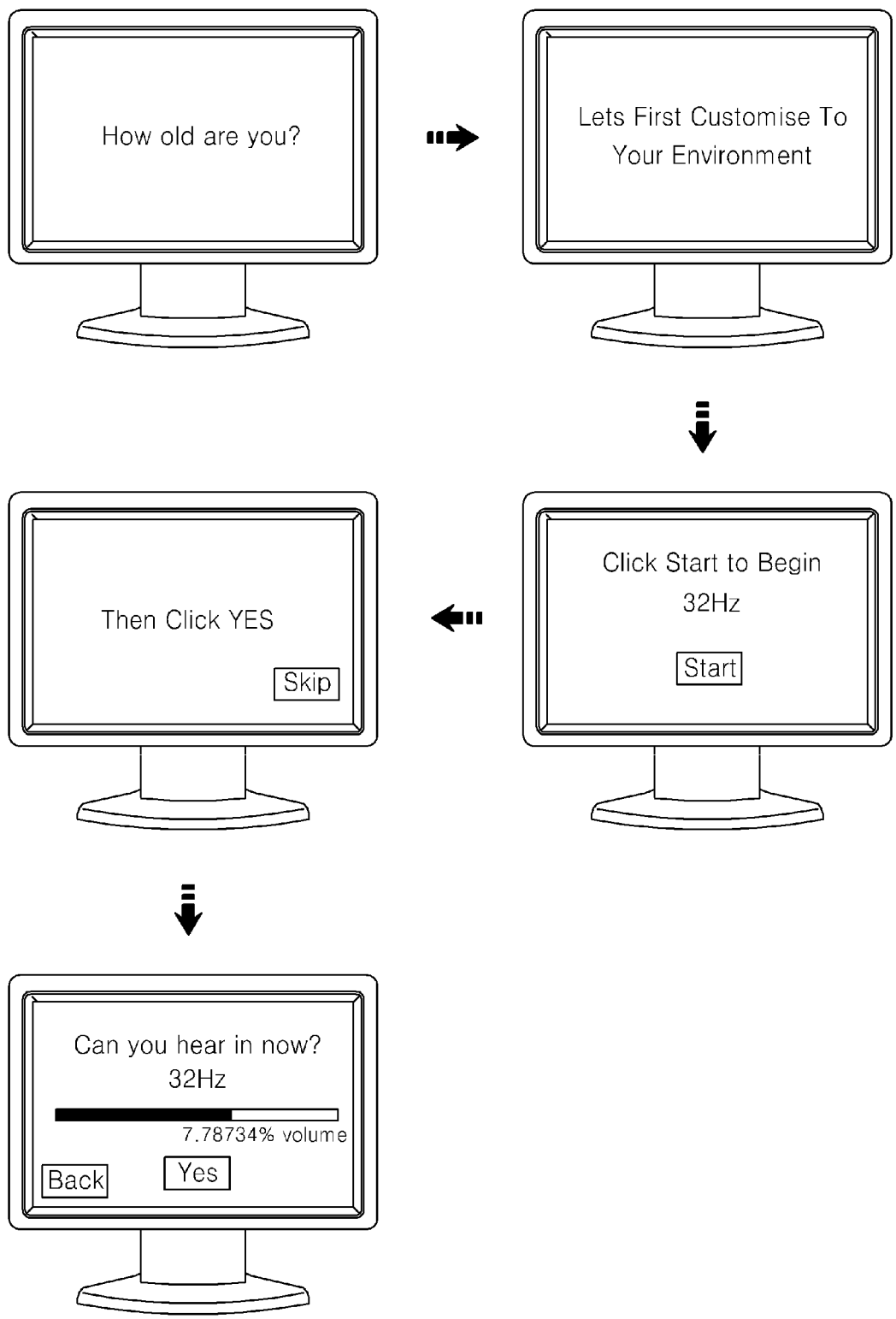
FIG. 3 is a view showing the flow of an operation screen of an apparatus for controlling a personalized audio frequency equalizer according to an embodiment of the present invention.

FIG. 1 is a perspective view showing an apparatus for controlling a Personalized audio frequency equalizer according to an embodiment of the present invention, FIG. 2 is a block diagram showing the configuration of an apparatus for controlling a Personalized audio frequency equalizer according to an embodiment of the present invention, and FIG. 3 is a view showing the flow of an operation screen of an apparatus for controlling a Personalized audio frequency equalizer according to an embodiment of the present invention.

As is known, an equalizer is an apparatus for adjusting a received signal by controlling relative strength of each frequency band. That is, it is a device which corrects sound quality by dividing the frequencies in a band of an audible range that a human being may hear with ears.

Therefore, the present invention provides an apparatus capable of measuring hearing ability of a user and automatically adjusting an audio frequency equalizer personalized to the hearing ability of the user.

To this end, an apparatus for controlling a personalized audio frequency equalizer of the present invention, which controls an audio frequency equalizer in an audio device from which a sound source is outputted, is implemented as a computer as shown in FIG. 1. Although the apparatus is shown as a desktop PC in the figure, various computing devices, such as a smart phone, a notebook PC, a tablet PC and the like, in addition to the desktop PC, may be used as the apparatus for controlling a personalized audio frequency equalizer of the present invention.

Inputs of all main-stream hardware media, such as a 3.5 mm auxiliary circuit headphone, may be supported by applying software techniques to a complementary hardware device that is connected to an auxiliary port of the apparatus for controlling a personalized audio frequency equalizer of the present invention or internally connected to a personal media device in the future through hardware.

The apparatus for controlling a personalized audio frequency equalizer of the present invention may include a user's hearing ability measurement unit 110, a personalized equalizer creation unit 120, and a sound source output unit 130 as shown in FIG. 2.

The user's hearing ability measurement unit 110 is a unit for measuring a value of volume that a user may hear by measuring hearing ability of the user for each frequency. That is, the user's hearing ability measurement unit 110 measures a HTUHD and an application test user hearing data (STUHD) that the user may hear by measuring the hearing ability of the user for each frequency. The volume value is measured for each frequency by increasing the volume at each frequency while the user wears a headphone and listen to audio through the headphone as shown in FIG. 1.

In two states of a plurality of system test frequencies, which are frequencies of a sound source adjusted on the hardware of an audio device, and a plurality of application test frequencies, which are frequencies of a sound source adjusted by the sound source playback software installed in the audio device, the user's hearing ability measurement unit 110 grasps an average volume that a user may hear for each of the system test frequencies and the application test frequencies by increasing the volume each having a test frequency. Here, the system test (system hardware test) refers to performing a test of a user's TOH on a final volume output through hardware amplification or decrease, and the application test (application software test) refers to performing a test of a user's TOH on the final volume output through digital amplification or decrease.

Grasping a minimum HTUHD means measuring, for each system test frequency, a value of volume that a user may hear when a volume having a system test frequency is outputted. In addition, an average of the measured system test user hearing data, i.e., an average of the system HTUHD, is calculated as a system test frequency average volume value, i.e., a hearing average value. In addition, the application STUHD, which is a value of minimum volume that the user may hear, is grasped for each application test frequency while increasing a volume having an application test frequency, in a state that system volume optimization of maintaining the HTUHD average value is accomplished on the hardware of the audio device.

Here, the system test frequencies may be four frequencies of 64 Hz, 250 Hz, 1 kHz and 4 kHz, and the application test frequencies may be 32 Hz, 64 Hz, 125 Hz, 256 Hz, 512 Hz, 1024 Hz, 2 kHz, 4 kHz, 8 kHz and 16 kHz.

In the two type of frequency tests (volume platforms) like this, a sample sound of each frequency (a clear and audible output at a given frequency) is provided to the user to be used for reference.

The sample sound (a clear and audible output of a given frequency) is played back before the TOH of each frequency is measured for the STUHD and the HTUHD. The user may be accustomed to various sounds of white tone that should be distinguished and may provide a further correct response. However, since the user may experience a phenomenon of 'after-vibration' or short-term tinnitus owing to the relatively big loudness of the sample sound, the user may recognize a sound that is not outputted due to continued vibrations, which may affect the accuracy of the result. This phenomenon may be corrected by creating a delay time between the sample sound and the real test at each frequency of all the UHDs, and this may remove the effect of vibration.

Each frequency is outputted with increasing volume from either volume platform (hardware/software), using a proprietary mechanism. Such a mechanism considers volume of a given frequency and an amount of time increase in relation to an average sensitivity of human being and a test time of a measured frequency. Therefore, the accuracy is enhanced and the time is reduced compared with an existing commercial hearing test. If the user responses that he or she can hear the tone, finally outputted system volume and application volume are stored. In addition, when a test is performed on a volume platform (hardware/software), the other volume platforms (hardware/software) should be maintained constant during the test.

Furthermore, when hearing ability of a user is measured, it may be implemented such that the user's age is grasped by inquiring the age of the user, and a volume value is not grasped for a test frequency that cannot be heard at the age of the user due to his/her physical conditions. This is not to measure the hearing ability at the frequency of 16 kHz when the user having the hearing test is 19 years of age or older since a human being is less sensitive to 16 kHz and cannot hear the sound after a specific age (about 19 years of age).

As a result, when the user's hearing ability measurement unit 110 measures hearing ability of a user as described above, screens such as an age inquiry screen, a system volume optimization screen, a frequency-specific measurement screen and the like are displayed as shown in the example screens of FIG. 3.

The personalized equalizer creation unit 120 creates a personalized equalizer considering the HTUHD and the application test user hearing data (STUHD).

The sound source output unit 130 outputs a sound source through the personalized equalizer created at a personalized equalizer creation step (step S530).

Hereinafter, the steps of creating a personalized audio frequency equalizer of the present invention will be described in detail.

Figure 4:
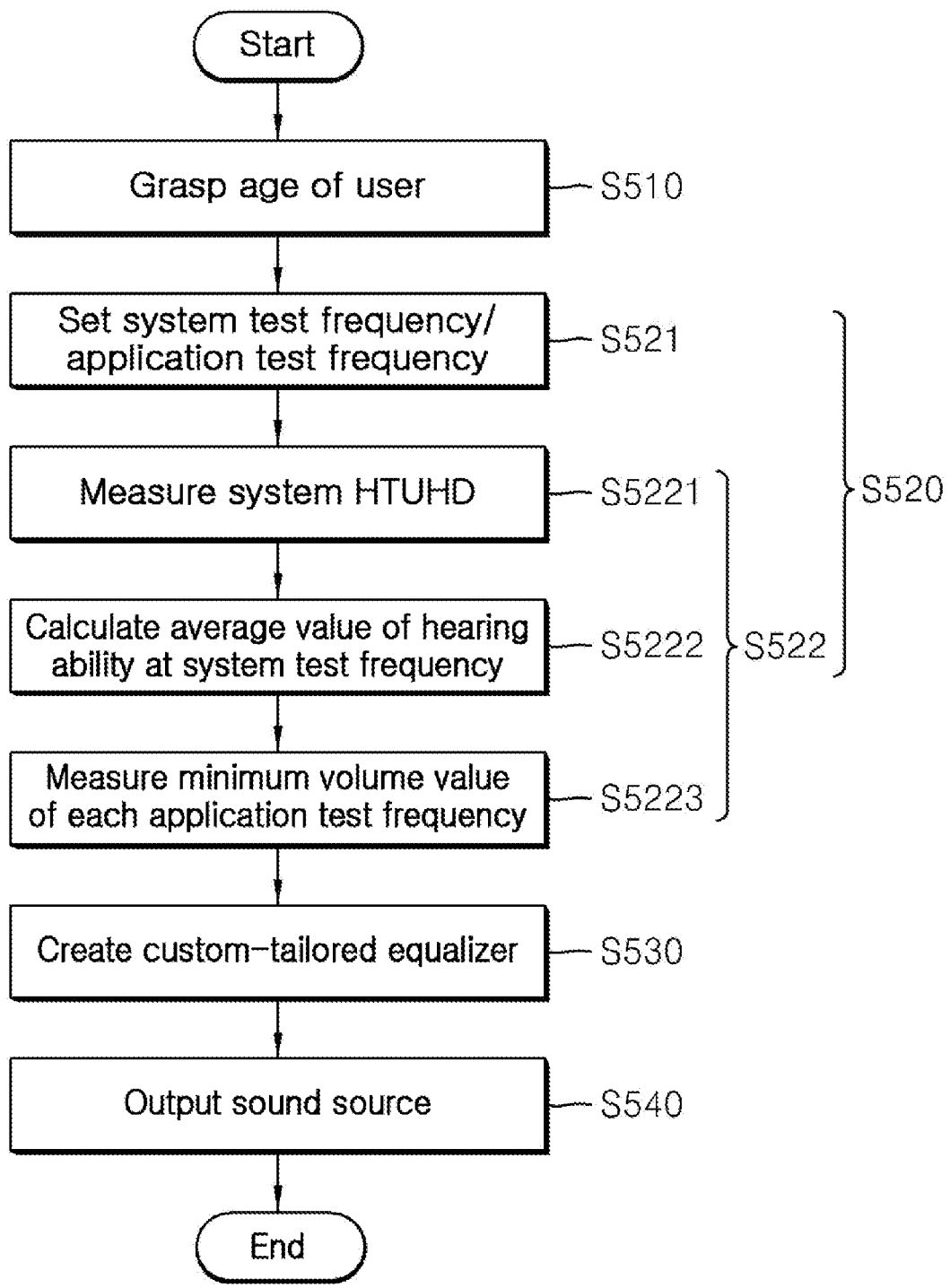
FIG. 4 is a flowchart illustrating a method of controlling a personalized audio frequency equalizer according to an embodiment of the present invention.
Figure 5:
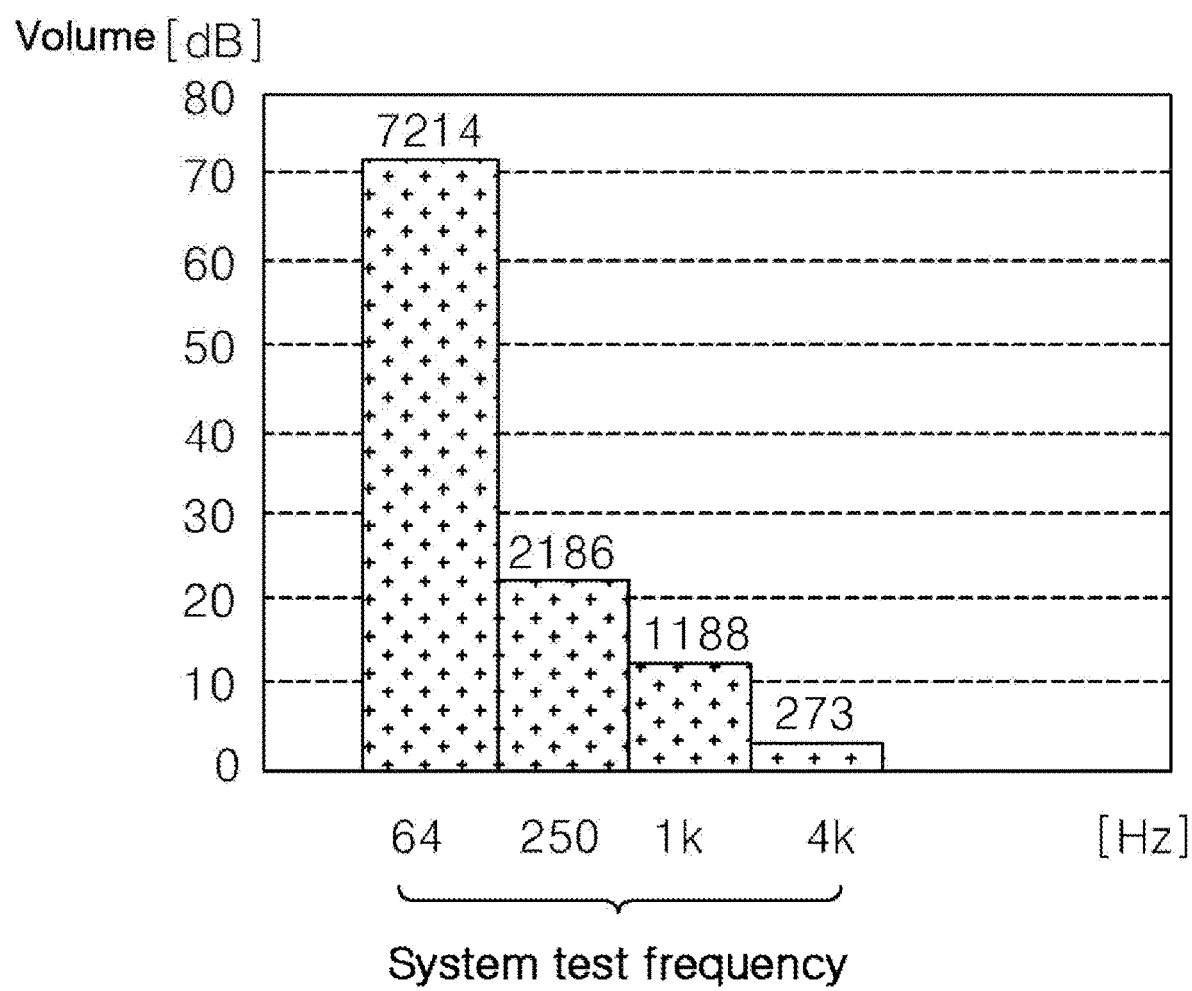
FIG. 5 is a graph showing volume values measured for each system test frequency according to an embodiment of the present invention.
Figure 6:
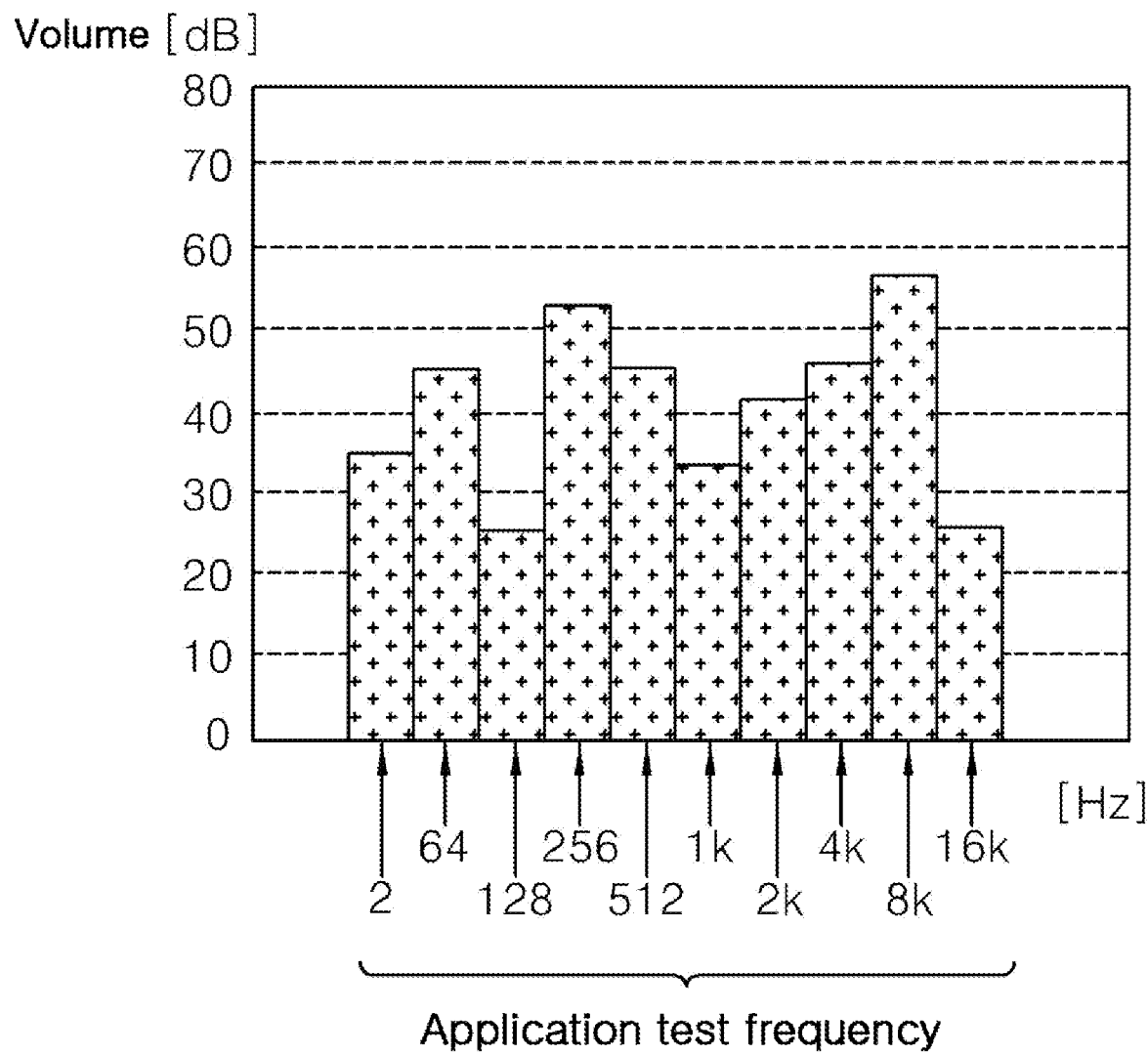
FIG. 6 is a view showing volume values measured for each application test frequency according to an embodiment of the present invention.

FIG. 4 is a flowchart illustrating a method of controlling a personalized audio frequency equalizer according to an embodiment of the present invention, FIG. 5 is a graph showing volume values measured for each system test frequency according to an embodiment of the present invention, and FIG. 6 is a view showing volume values measured for each application test frequency according to an embodiment of the present invention.

A method of controlling a personalized audio frequency equalizer of the present invention, which controls an audio frequency equalizer in an audio device from which a sound source is outputted, may include a user's age grasping step (step S510), a user's hearing ability measurement step (step S520), a personalized equalizer creation step (step S530), and a sound source output step (step S540) as shown in FIG. 4.

The user's age grasping step (step S510) is a step of grasping a user's age by inquiring the age of the user. It is not to grasp the volume value by grasping the user's age. It is to identify if the user's age, and thus implied physical conditions, will prevent him/her from hearing 16 kHZ at all.

If the user is above 19 years of age, an option of skipping 16 kHz may be provided. Since most of commercial earphones and headphones (personal media devices) have a difference in the frequency response and reduce the output of 16 kHz, the user often cannot hear the sound at all regardless of age. Although a sound is heard, if the sound goes out of the scope (changes as much as 9.5 dB or more) of the equalizer and the user does not sense it for a long time, it is more efficient to completely skip the frequency. Even in this case, the user may still hear the 16 kHz sound from the sample sound owing to amplification of system volume if he/she is below 19 years of age. Furthermore, the method of controlling a personalized audio frequency equalizer may calculate and store, for each frequency, an average of values of volume that the users in each age group may hear. Accordingly, this may be used for collecting data on the hearing ability of a specific age group, for example, may be used as a basic data for manufacturing hearing aids customized for specific age groups.

The user's hearing ability measurement step (step S520) is a step of measuring a value of volume that a user may hear for each frequency by measuring the hearing ability of the user for each frequency.

To this end, the user's hearing ability measurement step (step S520) may have a test frequency setting step (step S521) and a minimum user's hearing ability grasping step (step S522).

The test frequency setting step (step S521) is a step of setting a plurality of frequencies as test frequencies.

The present invention uses a plurality of system test frequencies, which are frequencies of a sound source adjusted on the hardware of an audio device. The present invention also uses a plurality of application test frequencies, which are frequencies of a sound source adjusted by the sound source playback software installed in an audio device, as test frequencies. Here, the system refers to hardware for adjusting volume of a sound source in an audio device, and the application refers to a software program executed in an audio device to play back a sound source.

This is to measure the hearing ability correctly by differentiating the system volume and the application volume. It is to measure the hearing ability considering a volume control matrix of the system volume and the application volume. A result more correct than that of an existing commercial hearing test may be obtained by measuring all major volume control platforms including the system volume and the software (application program control) volume. This is a process of primarily setting system volume using a system test frequency to perform an initial correction for general hearing ability of a user and environmental noises before making a further detailed measurement. An effect of saving time and the like may be obtained by performing a personalized measurement on the hearing ability using an application test frequency for a precise test after mainly compensating for the environmental noises and matching sensitivity of the user to general sound.

The system test frequencies like this may be four frequencies of 64 Hz, 250 Hz, 1 kHz and 4 kHz. In addition, the application test frequencies may be set to be ten frequencies of 32 Hz, 64 Hz, 125 Hz, 256 Hz, 512 Hz, 1024 Hz, 2 kHz, 4 kHz, 8 kHz and 16 kHz. Frequencies starting from 32 Hz and doubled up to 16 kHz (except 125 Hz) to cover the audible spectrum of a human being are used as the application test frequencies.

The minimum user's hearing ability grasping step (step S522) is a step of grasping a value of the smallest general system volume the user can hear the hardware test frequencies in a constant software volume unique per hardware test frequency.

Describing in detail, the minimum user's hearing ability grasping step (step S522) includes a system HTUHD measurement step (step S5221), a system test frequency hearing ability average value calculation step (step S5222), and an application test frequency-specific minimum volume value measurement step (step S5223).

The system HTUHD measurement step (step S5221) is a step of measuring a HTUHD that a user may hear for each system test frequency when a volume having a system test frequency is outputted.

It is calculating the minimum value of volume that a user may hear for each of the four system test frequencies of 64 Hz, 250 Hz, 1 kHz and 4 kHz.

For example, the apparatus outputs a sound volume having a system test frequency of 64 Hz, waits for a user response while gradually increasing the volume, and determines a volume value at the moment when the user responses that the sound is heard as the volume value of 64 Hz. In the same manner, the apparatus outputs a sound volume having a system test frequency of 250 Hz, waits for a user response while gradually increasing the volume, and determines a volume value at the moment when the user responses that the sound is heard as the volume value of 250 Hz. In addition, the apparatus outputs a sound volume having a system test frequency of 1 kHz, waits for a user response while gradually increasing the volume, and determines a volume value at the moment when the user responses that the sound is heard as the volume value of 1 kHz. In addition, the apparatus outputs a sound volume having a system test frequency of 4 kHz, waits for a user response while gradually increasing the volume, and determines a volume value at the moment when the user responses that the sound is heard as the volume value of 4 kHz.

Accordingly, a value of minimum audible volume may be grasped for each of the system test frequencies of 64 Hz, 250 Hz, 1 kHz and 4 kHz as shown in FIG. 5.

For reference, the reason of setting the system test frequencies to four frequencies of 64 Hz, 250 Hz, 1 kHz and 4 kHz is that the frequencies are equally spread out from the center of the spectrum, and a simplified version of the hearing spectrum of a human being may be appropriately expressed by using the frequencies to be multiplexed at regular intervals (e.g., 250×4=1000, 1000×4=4000).

The system test frequency hearing ability average value calculation step (step S5222) is a step of calculating an average of the measured system test user hearing data as a system test hearing average value. For example, when the minimum volume value is 8 [dB] at 64 Hz, the minimum volume value is 6 [dB] at 250 Hz, the minimum volume value is 6 [dB] at 1 kHz, and the minimum volume value is 12 [dB] at 4 kHz as a result of measuring the hearing ability of user 'Gildong Hong', the system test frequency average volume value becomes (8+6+6+12)/4=8 [dB].

The application test frequency-specific minimum volume value measurement step (step S5223) is a step of grasping an application STUHD. It may be obtained by finding the smallest software volume the user can hear per application test frequency in a constant system volume set on the hardware of the audio device.

That is, it is grasping a minimum audible volume value for each of the ten application test frequencies of 32 Hz, 64 Hz, 125 Hz, 256 Hz, 512 Hz, 1024 Hz, 2 kHz, 4 kHz, 8 kHz and 16 kHz from the aspect of software which adjusts the sound volume by software while maintaining the output of system volume to be the system test hearing average value.

For example, the apparatus outputs a sound volume having an application test frequency of 32 Hz, waits for a user response while gradually increasing the volume, and determines a volume value at the moment when the user responses that the sound is heard as the volume value of 32 Hz. In the same manner, the apparatus outputs a sound volume having an application test frequency of 64 Hz, waits for a user response while gradually increasing the volume, and determines a volume value at the moment when the user responses that the sound is heard as the volume value of 64 Hz. In the same manner, a volume value is determined for each of the other eight application test frequencies of 125 Hz, 256 Hz, 512 Hz, 1024 Hz, 2 kHz, 4 kHz, 8 kHz and 16 kHz.

Accordingly, as shown in FIG. 6, an audible volume value may be grasped for each of the ten application test frequencies of 2 Hz, 64 Hz, 125 Hz, 256 Hz, 512 Hz, 1024 Hz, 2 kHz, 4 kHz, 8 kHz and 16 kHz.

Meanwhile, before the user's hearing ability measurement step (step S520), the user's age grasping step (step S510) may have a step of grasping the user's age by inquiring the age of the user. This is not to grasp a minimum volume value in the case of a test frequency that cannot be heard at the age of the user due to the physical conditions.

Furthermore, the method of controlling a personalized audio frequency equalizer may calculate and store, for each frequency, an average of the minimum audible volume of the users in several ages.

Meanwhile, the personalized equalizer creation step (step S530) is a step of creating a personalized equalizer considering the volume value of each frequency.

When it is assumed that a standard volume value allocated and stored for each frequency is the standard hearing data (SHD), a frequency volume value used for system test is a system test user hearing data (hardware test user hearing data (HTUHD)), and a frequency volume value used for application test is an application test user hearing data (software test user hearing data (STUHD)), a personalized equalizer complementing for a difference between the user hearing data (UHD) and the SHD is created using the HTUHD and the application test user hearing data (STUHD), and hearing ability almost close to the ideal hearing ability and indicated by the SHD is given to the user.

The sound source output step (step S540) outputs a sound source through the personalized equalizer created at the personalized equalizer creation step (step S530). Accordingly, a sound source may be outputted by automatically controlling the equalizer on the basis of the user's hearing ability so that a sound similar to the standard hearing data (SHD) may be heard through the created personalized equalizer.

Meanwhile, the method of creating a personalized equalizer may be accomplished as shown below in the two types of embodiments.

A first method of creating a personalized equalizer may have the steps of calculating an average of minimum volume value measured for each application test frequency as an application test frequency average volume value; calculating an average of standard volume value of each frequency as a standard average volume value; calculating an error volume value by subtracting the application test frequency average volume value from the standard average volume value; calculating a correction volume value for each frequency by adding the calculated error volume value to each test frequency minimum volume value; and determining the correction volume value of each frequency through the personalized equalizer.

A second method of creating a personalized equalizer may have the steps of calculating an error volume value for each frequency by subtracting the standard volume value from the minimum volume value of the application test frequency for each frequency; calculating an average of minimum volume value measured for each application test frequency as an application test frequency average volume value; calculating a correction volume value for each frequency by subtracting the application test frequency average volume value from the error volume value; and determining the correction volume value of each frequency through the personalized equalizer.

Accordingly, the equalizer may be automatically controlled through the first method of the second method of creating a personalized equalizer so that a sound similar to the standard hearing data (SHD) may be heard.

The method of controlling a personalized audio frequency equalizer has a step of converting amplitude (a volume unit of a computer) of a sound source outputted from a computer into decibel through an equation of 'decibel=20×log 10 (amplitude)'.

The method of controlling a personalized audio frequency equalizer has a step of matching an average value of the STUHD and an average value of the SHD. This step is enabled by adding a difference between the STUHD average and the SHD average to each frequency of the UHD.

The method of controlling a personalized audio frequency equalizer has a step of subtracting an average value of the STUHD from the SHD for each frequency.

The method of controlling a personalized audio frequency equalizer has a step of subtracting an average value of the STUHD for each frequency.

If a frequency has a value larger than 9.5, the method of controlling a personalized audio frequency equalizer has a step of subtracting a value exceeding 9.5 at each frequency. For example, when the frequency value is 10, all frequency values are subtracted by 0.5, and the method has a subtraction step like this since a specific audio file is distorted due to excessive software amplification and this may induce an unpleasant experience.

Pre-amplification is set on the basis of 500 Hz and 1,000 Hz. The pre-amplification may prevent over-amplification and discontinuity of audio by controlling overall volume correction to an appropriate level. Frequently, 500 Hz and 1,000 Hz are the loudest or most emphasized frequencies in a music file, and in addition, since a human being is intrinsically most sensitive, the frequencies mentioned above are implemented to control the pre-amplification.

For reference, amplitude of a volume value is converted into decibel when a personalized equalizer is created, and since the apparatus may be overloaded during the measurement although the maximum value of amplitude is 1, an extreme and unrealistic decibel value can be prevented by limiting the maximum amplitude data to 0.98.

In addition, since the white noise played back while measuring the HTUHD and the STUHD is temporarily paused and resumed at regular intervals regardless of an elapsed time, the effect of delusion by tinnitus is further reduced. This is to allow a user to more easily and correctly distinguish the white noise in contrast to surrounding sounds and "after effects" sound following from previously emitted sounds. The effect of the procedure on the required time is that the frequency is short and minimized to be similar to a short and constant warning sound since the temporarily paused time is minimized but still offer a significant improvement to the quality of the test. If the volume increment is increased, the total duration time of the temporary pause may be recognized and compensated for each frequency.

According to an embodiment of the present invention, as a personalized equalizer for confirming hearing ability of a user and compensating for the hearing ability using the SHD by customizing the frequencies in a range of 32 Hz to 16 kHz is provided, possibility of hearing loss is lowered, and satisfaction of enjoying audio and music is enhanced.

In addition, since the system volume and the application volume are separately tested, the personalized audio frequency equalizer maximizes accuracy and precision.

In addition, when STUHD are collected in a system volume test, since the application volume level is considered after a predetermined time is elapsed from the beginning of a given frequency test when an application test is executed, tinnitus can be prevented.

The embodiments in the description of the present invention described in detail are the most preferable examples selected and presented among various possible examples to help understanding of those skilled in the art, and the spirit of the present invention is not necessarily limited or restricted by the embodiments, and various changes and modifications and equivalent other embodiments are possible without departing from the spirit of the present invention.

What is claimed is:

1. A method of controlling a personalized audio frequency equalizer by an audio device for outputting a sound source, the method comprising:
   (a) receiving a user's age by an input of a user via a user interface;
   (b) setting a plurality of frequencies as test frequencies, including
      (b1) setting a plurality of system test frequencies, which are frequencies of a sound source adjusted on hardware of the audio device,
      (b2) setting a plurality of application test frequencies, which are frequencies of a sound source adjusted by sound source playback software installed in the audio device, and
      (b3) excluding a preset frequency from the test frequencies if the user's age input by the user is equal to or greater than a preset age;
   (c) measuring, for each test frequency, a minimum audible volume which the user is able to hear, including
      (c1) measuring, for each system test frequency, the minimum audible volume as a system test user hearing data (HTUHD) that the user is able to hear when a test sound having a system test frequency is outputted,
      (c2) calculating an average of the system test user hearing data (HTUHD) measured for each system test frequency as a system test hearing average value, and
      (c3) measuring, for each application test frequency, the minimum audible volume as an application test user hearing data (STUHD) that the user is able to hear while maintaining the system test hearing average value on the hardware of the audio device and increasing a volume of a test sound having an application test frequency adjusted by the sound source playback software;
   (d) creating the personalized equalizer using the system test user hearing data (HTUHD) and the application test user hearing data (STUHD); and
   (e) outputting a sound source through the personalized equalizer created at the step (d).

2. The apparatus according to claim 1, wherein the step (c1) includes
   increasing a volume of the test sound for each test frequency, and
   setting a volume value input by the user for each test frequency as the minimum audible volume of each system test frequency.

3. The apparatus according to claim 2, wherein the plurality of system test frequencies include 64 Hz, 250 Hz, 1 kHz and 4 kHz, and the plurality of application test frequencies include 32 Hz, 64 Hz, 125 Hz, 256 Hz, 512 Hz, 1024 Hz, 2 kHz, 4 kHz, 8 kHz and 16 kHz, and wherein the preset frequency excluded from the test frequencies if the user's age input by the user is equal to or greater than a preset age includes 16 kHz.

4. An apparatus for controlling a personalized audio frequency equalizer, the apparatus comprising:

a computing device configured to:

receive a user's age information input via a user interface;

set a plurality of system test frequencies, which are frequencies of a sound source adjusted on hardware of an audio device, as test frequencies;

set a plurality of application test frequencies, which are frequencies of a sound source adjusted by sound source playback software installed in the audio device, as the test frequencies;

exclude a preset frequency from the test frequencies if the user's age input by the user is equal to or greater than a preset age;

measure, for each system test frequency, a minimum audible volume as a system test user hearing data (HTUHD) that the user is able to hear when a test sound having a system test frequency is outputted;

calculate an average of the system test user hearing data (HTUHD) measured for each system test frequency as a system test hearing average value;

measure, for each application test frequency, a minimum audible volume as an application test user hearing data (STUHD) that the user is able to hear while maintaining the system test hearing average value on the hardware of the audio device and increasing a volume of a test sound having an application test frequency adjusted by the sound source playback software;

create the personalized equalizer using the system test user hearing data (HTUHD) and the application test user hearing data (STUHD); and output a sound source through the personalized equalizer via a speaker.

5. The apparatus according to claim 4, wherein the plurality of system test frequencies include 64 Hz, 250 Hz, 1 kHz and 4 kHz, and the plurality of application test frequencies include 32 Hz, 64 Hz, 125 Hz, 256 Hz, 512 Hz, 1024 Hz, 2 kHz, 4 kHz, 8 kHz and 16 kHz, wherein the preset frequency excluded from the test frequencies if the user's age input by the user is equal to or greater than a preset age includes 16 kHz.

6. The apparatus of claim 4, wherein, to measure the system test user hearing data (HTUHD), the computing device is configured to:

increase a volume of the test sound for each test frequency, and set a volume value input by the user for each test frequency as the minimum audible volume of each system test frequency.

* * * * *